United States Patent [19]

Powers

[11] Patent Number: 5,095,910
[45] Date of Patent: Mar. 17, 1992

[54] ULTRASONIC IMAGING OF BIOPSY NEEDLE

[75] Inventor: Jeffry E. Powers, Lake Stevens, Wash.

[73] Assignee: Advanced Technology Laboratories, Inc., Bothell, Wash.

[21] Appl. No.: 511,382

[22] Filed: Apr. 18, 1990

[51] Int. Cl.$^5$ ................................................. A61B 8/12
[52] U.S. Cl. ................................................. 128/662.05
[58] Field of Search .................. 128/24 A, 662.05; 604/22

[56] References Cited

U.S. PATENT DOCUMENTS

| | | | |
|---|---|---|---|
| 3,556,079 | 1/1971 | Omizo | 128/24 A |
| 3,570,476 | 3/1971 | Oregg | 128/24 AA |
| 3,805,787 | 4/1974 | Banbo | 128/24 AA |
| 4,249,538 | 2/1981 | Vilkomerson et al. | 128/662.05 |
| 4,407,294 | 10/1983 | Vilkomerson | 128/662.05 |
| 4,428,379 | 1/1984 | Robbins et al. | 128/662.05 |
| 4,431,006 | 2/1984 | Trimmer et al. | 128/662.05 |
| 4,816,018 | 3/1989 | Porisi | 604/22 |

OTHER PUBLICATIONS

"Motion Marking in Color Doppler Ultrasound Needle and Catheter Visualization", T. Kurohiji et al., J Ultrasound Med 9:243–45, 1990.

*Primary Examiner*—Francis Jaworski
*Attorney, Agent, or Firm*—W. Brinton Yorks, Jr.

[57] ABSTRACT

A system for imaging a biopsy needle with ultrasound is shown in which the needle tip elicits a Doppler response through controlled reciprocation of the needle tip. In a preferred embodiment the biopsy needle includes a hollow cannula which carries a removable stylet. Means for reciprocating the stylet is coupled to the proximal end of the stylet, and the distal tip of the stylet is reciprocated at the distal end of the cannula. This motion is detected through Doppler interrogation of the body region at which the biopsy is to be performed, and the Doppler response of the needle tip in the image of the body region allows the needle tip to be monitored as it approaches the tissue to be biopsied.

15 Claims, 3 Drawing Sheets

ULTRASONIC IMAGING OF BIOPSY NEEDLE

This invention relates to ultrasonic imaging systems and, in particular, to the imaging of biopsy needles by ultrasonic imaging systems during surgical biopsy procedures.

Surgical biopsy procedures are commonly performed with the assistance of ultrasonic imaging to enable the physician to view the tissue being biopsied. It is of course desirable during such procedures to be able to clearly visualize the needle and monitor its progression through the body as it approaches the tissue mass from which a sample is to be taken. Accessories to assist the physician in such procedures are readily available such as biopsy needle guides to be used in conjunction with a transducer scanhead. A conventional needle guide attaches to the scanhead to direct the needle to the sector or area of view of the scanhead, thereby mandating that insertion of the needle will follow a path that is confined to the area of the body being imaged. Other techniques to more clearly distinguish the needle in the ultrasonic image have also been suggested, such as the formation of a diffraction grating on the needle. The diffraction grating is designed to cause the returning ultrasonic echoes from the needle to be more intense, and hence more readily distinguishable than would otherwise be the case.

A series of patents including U.S. Pat. Nos. 3,556,079; 4,249,539; 4,431,006; 4,407,294; and 4,428,379 have suggested an active approach to ultrasonically imaging a biopsy needle. In these patents an ultrasonic transducer is attached to the biopsy needle to cause the needle to transmit and/or receive ultrasonic waves in cooperation with an imaging scanhead. In the various configurations shown in these patents the transducer is attached to the proximal (external) end of the needle and the needle becomes a conductor of ultrasound, or the transducer is physically located at the distal tip of the needle or a stylet carried within the needle. To varying degrees the techniques discussed in these patents enable the tip of the needle to be sharply visualized in the ultrasonic image by reason of the presence of the active transducer element in association with the needle, and particularly when it is located at the needle tip. These techniques have two significant drawbacks, however. One is the construction of a highly miniaturized transducer for in vivo use, and the accompanying concerns for patient safety. The second is the need for significant system integration required to synchronize signals to and from the biopsy needle transducer with the signals of the imaging scanhead. While potentially offering the advantages of high needle visibility and precision, these active and invasive techniques pose significant implementation dilemmas.

The principles of a technique for passively visualizing a biopsy needle was recently reported in the Journal of Ultrasound in Medicine, Vol. 9, at pp 243-45 (1990). There it was noted that the passage of biopsy needles or their guide wires was distinctly evident on color Doppler images as the needle or guide wire was being moved. Hand manipulation of a biopsy needle or guide wire, it was found, provided a color image that corresponded to the shaft of the needle. Such a technique is inherent in the physical principles of Doppler imaging, and is in many cases preferable to the above active techniques by reason of its simplicity and lack of need for additional system integration. The technique suffers shortcomings in that the image of the needle is only highly defined when the needle is being manipulated, and is a coarse representation of the entire needle shaft. It would be preferable to be able to continually visualize only the tip of the needle, to better localize the proximity of the needle tip to the tissue which is to be biopsied.

In accordance with the principles of the present invention, an apparatus and method are presented for ultrasonically imaging a biopsy needle. The present invention is advantageous as compared with the aforementioned active techniques in that no invasive transducers are employed and system integration may be minimized. The present invention is also advantageous as compared with the aforementioned technique of hand manipulating the needle in that the tip of the biopsy needle is preferentially and continuously visualized. An apparatus constructed in accordance with the principles of the present invention employs means for mechanically reciprocating a biopsy needle, and preferably a stylet carried by a biopsy needle. In a preferred embodiment the frequency of reciprocation is a low audible frequency. Such mechanical reciprocation causes low amplitude motion at the tip of the needle, which is readily detectable by use of Doppler techniques. The detected mechanical motion at the needle tip is translated by Doppler detection into locational representation of the needle tip in the image of the tissue being biopsied. In the method of the present invention means for mechanically reciprocating a biopsy needle or stylet is connected to the needle or stylet. The needle or stylet motion is detected by a Doppler imaging system as the biopsy procedure is being performed.

It has been found that unsynchronized reciprocation of the biopsy needle or stylet can cause a constantly changing Moire pattern when the Doppler representation of the needle tip is displayed in color. In accordance with a first aspect of a preferred embodiment of the present invention, the cycle reciprocation of the needle or stylet is synchronized with the Doppler scanning sequence. This enables the needle tip to be displayed in a constant hue of a predetermined color for positive identification of the needle tip in an ultrasonic image of the tissue structure.

It has further been found that when the needle tip is represented by its Doppler signal response, the representation of the needle tip can obscure the structural image of the tissue which is to be biopsied. This will impair the ability of the physician to precisely locate the needle tip in proximity to the target tissue. In accordance with a further aspect of a preferred embodiment of the present invention, the representation of the Doppler signal response of the needle tip provides a color modulation of the image of the tissue structure. Thus, the target tissue is at all times visible to the physician and is not obscured by the Doppler signal response of the needle tip, and the hue and intensity of the color of the target tissue provides a precise indication of the proximity of the needle tip to the target tissue.

Figure 1:
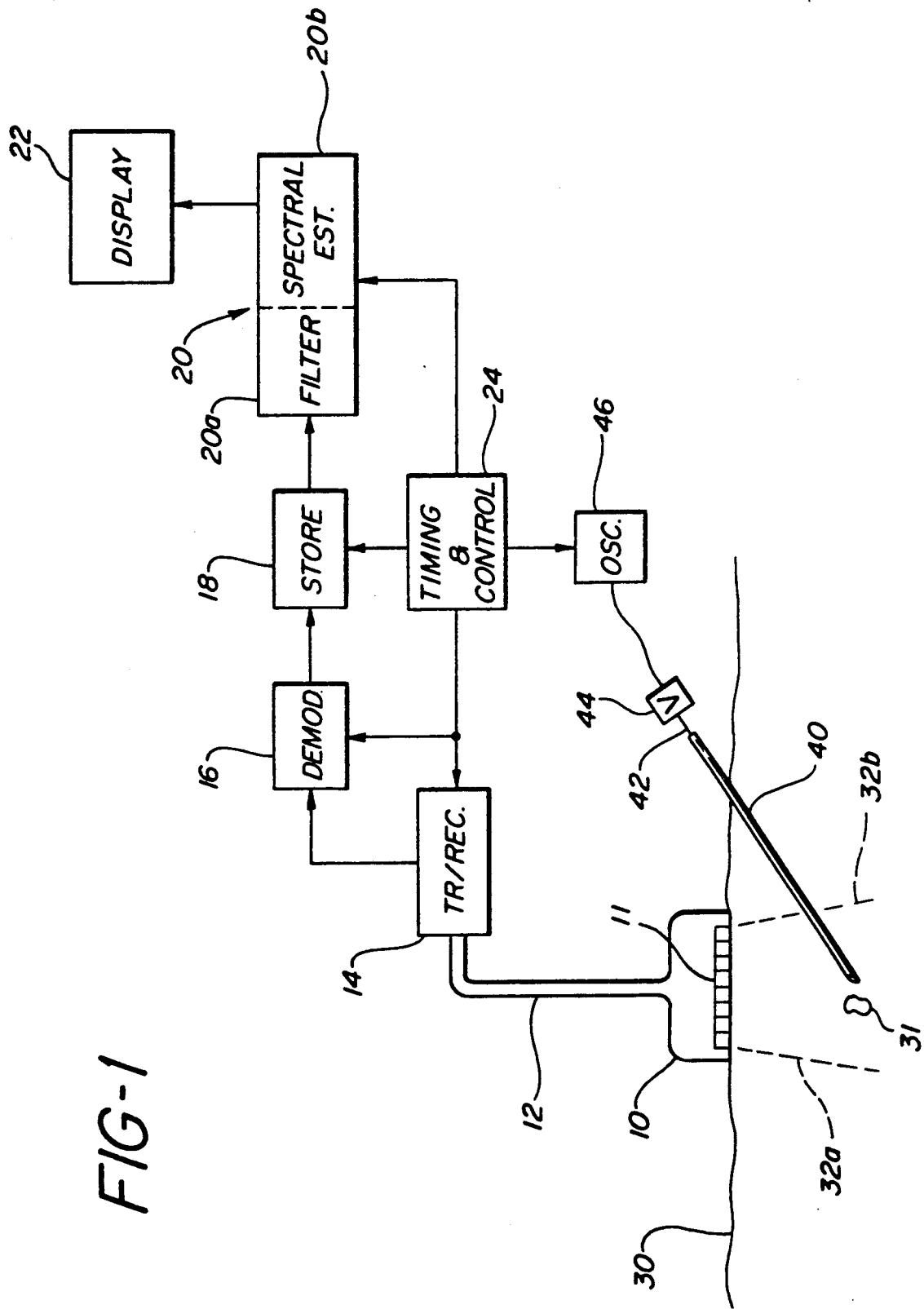
FIG. 1 illustrates in block diagram form a system for ultrasonically imaging a biopsy needle in accordance with the principles of the present invention.

Referring first to FIG. 1, a system for ultrasonically imaging a biopsy needle in accordance with the present invention is illustrated in block diagram form. An ultrasonic scanhead 10 including a plurality of imaging transducers 11 is in contact with the surface 30 of the skin of a patient. In the preferred embodiment the scanhead 10 is a phased array scanning transducer device. The scanhead is connected by a cable 12 to a transmitter and receiver module 14, which provides drivers for supplying energizing pulses or waves to the transducers 11, and receivers for receiving and amplifying electrical signals produced by the transducers in response to the reception of echoes and return signals from the tissue structure being scanned. The transducers of the scanhead are energized in a sychronized manner to generate phased array ultrasonic waves under control of a timing and control system 24 connected to the transmitting and receiving module 14. The received and amplified electrical signals are demodulated to system baseband signals by a demodulator 16, then stored in a memory or store 18 in positional correspondence to the rays or vectors of interrogation of the phased array scanhead. The stored signals are then supplied to a processor 20, where they are filtered by a high pass filter 20a and analyzed by a spectral estimator 20b. The spectral estimator provides data which is analyzed for phase shift information as will be described in conjunction with FIG. 4 below, which information is then translated to positionally representative velocity display information, such as color. The display information is then displayed in the desired image format on a display 22. The elements thus far described are those of a color flow imaging system such as that employed in the Ultramark 9 color flow imaging system available from Advanced Technology Laboratories, Inc. of Bothell, Wash.

In accordance with the principles of the present invention a biopsy needle is provided, including a hollow cannula 40 with a tapered and pointed distal tip. Carried within the cannula as it is inserted into the tissue is a removable member 42 extending to the pointed tip, such as a stylet. The proximal end of the member 42 is coupled to a mechanism 44 which longitudinally reciprocates the member or stylet. The mechanism 44 may be any one of a variety of devices which generate linear reciprocating motion, such as a linear motor, solenoid, speaker coil, or other device capable of developing and coupling longitudinal reciprocating motion to the member 42. The mechanism 44 is energized by an oscillator 46 which develops an appropriate energizing waveform for the mechanism, such as a sine wave, pulse, sawtooth or other waveform. As will be described below, the oscillator waveform is synchronized with the energization of the transducers 11 of the scanhead by connection of the oscillator 46 to the timing and control system 24, thereby synchronizing the motion of the member 42 with the rays of the scanhead for clear and continuous visualization of the biopsy needle.

The method of using the biopsy needle of the present invention is as follows. The scanhead 10 is placed against the tissue surface 30 and maneuvered until the mass 31 to be biopsied is viewed in the image sector. The image sector is represented in FIG. 1 by the dashed sector boundaries 32a and 32b on either side of the mass 31. The mechanism 44 is connected to member 42 of the biopsy needle and energized to longitudinally reciprocate the member 42 within the cannula 40. The biopsy needle is then inserted into the tissue and directed toward the mass 31 and into the field of view of the scanhead. As the needle comes into the field of view, the motion of the vibrating member at the tip of the cannula causes a Doppler response by the imaging system. The Doppler response is indicated positionally in the structural ultrasound image as by a color spot or dot. The color spot or dot indicates the position of the motion of the member 42 at the cannula tip, and as the biopsy needle is directed toward the mass 31 the color spot will approach the mass 31 in the display image. When the color spot converges with the mass 31 in the image the cannula 40 is properly positioned to perform a biopsy of the mass. The member 42 is withdrawn from the cannula at that point to allow biopsy through the cannula.

Figure 2:
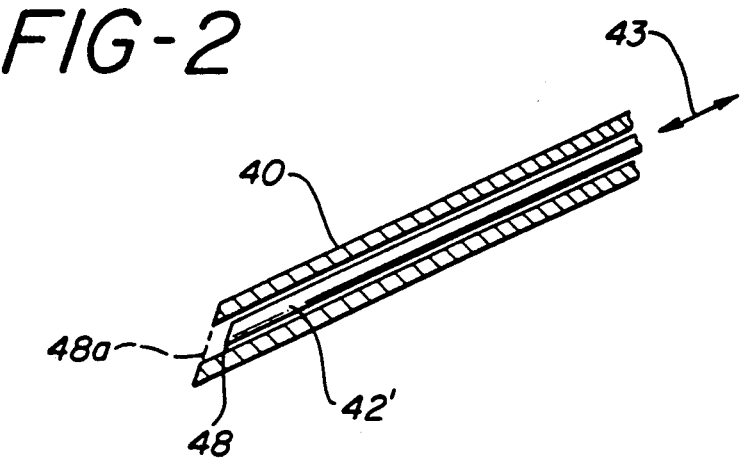
FIG. 2 is a cross-sectional view of the distal end of a biopsy needle constructed in accordance with the principles of the present invention.

The motion of the member 42 of the biopsy needle is more clearly shown in the enlarged view of the distal end of the needle in FIG. 2. In FIG. 2 a stylet 42' is reciprocated longitudinally within the cannula 40, as indicated by the arrow 43. Preferably the motion imparted to the stylet is confined in the longitudinal direction to as great a degree as possible. When radial vibration components are minimized, the Doppler response of the needle is substantially confined to the very tip of the needle, where the tip of the stylet is reciprocating between its retracted position as shown at 48 and its extended position as indicated by the dashed line at the cannula opening at 48a. In a constructed embodiment, the range of travel between positions 48 and 48a is only a few millimeters or less, and generally around one millimeter. Thus, what will appear in the ultrasonic image as a visual Doppler response is only the motion of the stylet at the open needle tip, to the exclusion of the body of the cannula. Since it is the needle tip that is to be maneuvered precisely to the tissue to be biopsied, it is preferable to have the needle tip highlighted in the image, which is accomplished if the only Doppler response is from the needle tip. Radial vibration components can cause motion of the cannula surface, which can undesirably elicit a Doppler response from various locations along the surface of the cannula 40 and hence visualization of this motion in the image in addition to that at the needle tip. This can present a confusing image to the user, who is trying to intently follow the path of the needle tip. By minimizing radial motion components and resulting Doppler responses from the cannula, the accuracy of the biopsy procedure is enhanced.

Moreover, by minimizing radial motion components in the needle, sensations of vibration are not transmitted into the tissue or the hand of the user. While radial vibration components will unavoidably occur when the needle is bent as it is inserted, a common practice, as the needle is straightened the sensation of vibration at the cannula surface is reduced.

In a preferred embodiment of the present invention, the greatest distal extension of the range of travel of the stylet is only to the open end of the cannula, and not beyond. It is desirable to avoid any potential damage to tissue which would be caused by reciprocating the stylet tip beyond the open cannula tip. The only cutting of tissue should be that done by the sharpened cannula tip under the controlled manipulation of the surgeon.

Figure 3:
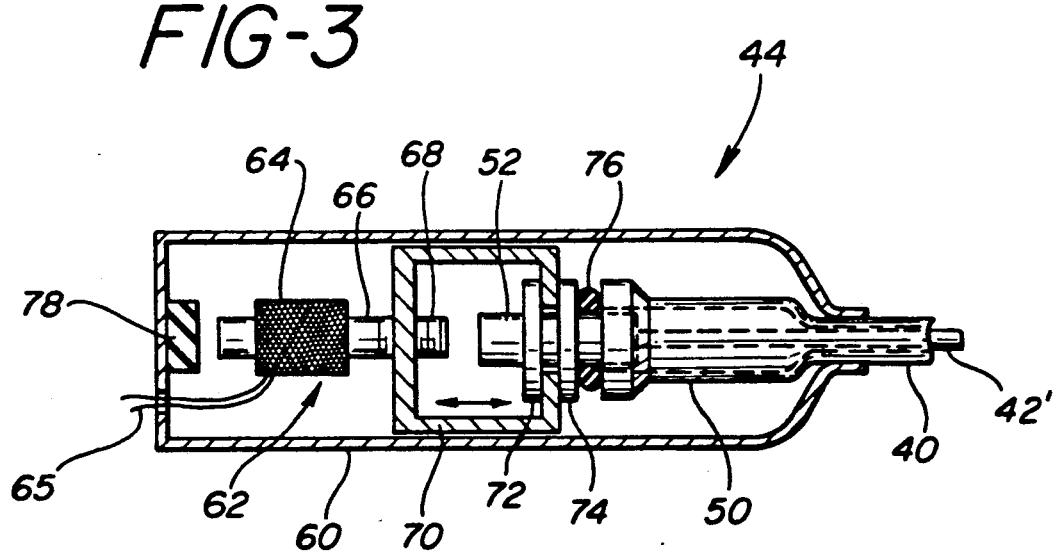
FIG. 3 is a cross-sectional view of a mechanism for vibrating a biopsy needle in accordance with the principles of the present invention.

A mechanism for longitudinally moving member 42 of the biopsy needle of FIG. 1 is shown in the cross-sectional view of FIG. 3 of the proximal end of the biopsy needle. Attached to the end of the cannula 40 is a cannula hub 50, and attached to the end of the stylet 42' is a stylet hub 52. Located around the stylet hub 52 are two spaced annular rings or flanges 72 and 74. This proximal end of the biopsy needle fits inside the housing 60 of the reciprocating mechanism. Inside the proximal end of the housing 60 is a solenoid 62, including a coil 64 and a movable plunger 66 which is threaded at the end 68. Wires 65 from the coil 64 exit from the rear of the housing 60. The threaded end of the plunger 66 threads into a reciprocating slider 70, which has an opening at its distal end that engages the stylet hub 52 between the rings 72. A rubber O-ring 76 forward of the flange 74 and a rubber bumper 78 rearward of the plunger assist the mechanism at turn-around.

In operation, the solenoid 62 is energized by an appropriate waveform to longitudinally reciprocate the plunger 66 within the coil 64. As the plunger reciprocates it moves the slider 70 as indicated by the arrow, thereby longitudinally reciprocating the stylet 42' within the cannula 40. The O-ring 76 and bumper 78 damp the motion of the mechanism when it reverses its direction.

Other mechanisms such as a linear motor may alternatively be employed to generate the desired reciprocating motion in place of the solenoid. A speaker coil arrangement may alternatively be employed, in which a coil is the moving component. In certain applications the speaker coil type of mechanism may be preferred, as it is the lower coil mass which is moving as opposed to the generally larger mass of a solenoid plunger.

Figure 4:
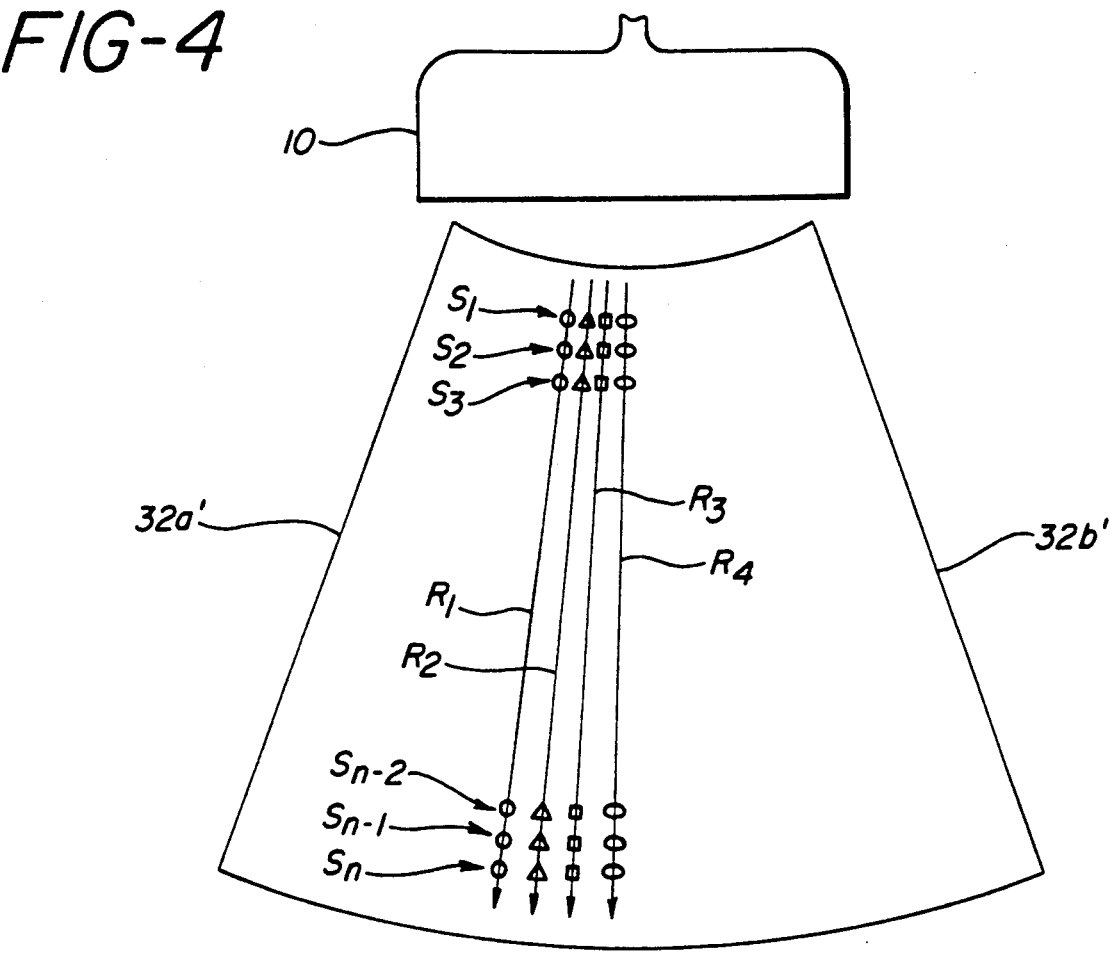
FIG. 4 is a representation of rays of an ultraxonic sector illustrating the principles of the present invention.
Figure 5A:
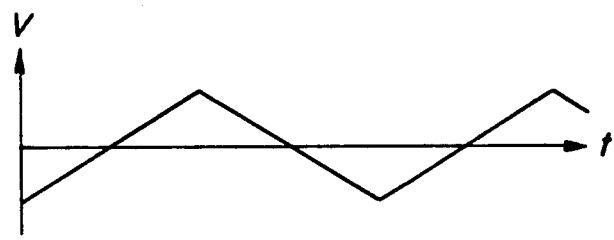
FIGS. 5a and 5b are a waveform and timing diagram illustrating operation of a biopsy needle of the present invention.
Figure 5B:
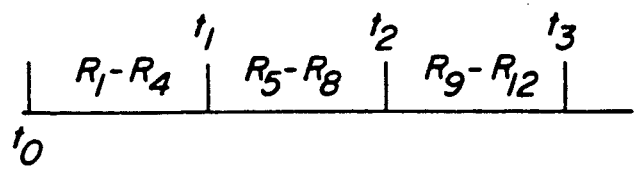

The use of the biopsy needle arrangement of the present invention with the preferred color flow imaging display system is explained with reference to FIGS. 4, 5a, and 5b. The color flow imaging system described with reference to FIG. 1 operates by transmitting a series of ultrasound pulses, called an ensemble. The ensemble of pulses is sent in a single direction, referred to as a ray line. Four such ray lines, R1, R2, R3, and R4, are illustratively shown in FIG. 4. Return signals from the ensemble of pulses are received, demodulated, and stored with respect to position along the ray line, as indicated by positions S1, S2, S3, ... Sn-2, Sn-1, of ray line R1 in FIG. 4. As the signals from ray line R1 are being processed a similar ensemble is transmitted and received for the next ray line R2. The processing includes high pass filtering of the signal information followed by spectral estimation. An important recognition of the present invention is that, although Doppler is commonly referred to by users as having a frequency or frequencies of operation, the spectral estimation does not measure a frequency; it determines a phase shift. It is only when the phase shift is divided by time and presented to the user in this format that a frequency translation is derived. The principle of the present invention is that the motion at the tip of the needle has a velocity of translation or range of translation between ray lines, and it is this velocity or range of translation which causes a Doppler response by a color flow imaging system. Contrary to what common belief would dictate, it is not the frequency of vibration of the needle which is being measured, but rather the Doppler shifted signals resulting from translation of the needle tip. In practice, a number of ray line ensembles are transmitted, received and processed, such as those of ray lines R1, R2, R3, and R4 of FIG. 4. Signal response across the ray lines, as indicated by the arrows extending from S1, S2, S3, etc. are then analyzed for Doppler shift indicative of motion, and motion is then displayed positionally with color and intensitity representative of direction and velocity of motion.

It has been found that when the stylet tip is moved asynchronously with respect to the color flow imaging system operation, a moving or flickering Moire pattern will develop in the color spot representative of the motion at the needle tip. The color will flicker or change as motion changes with respect to the ray line timing from one direction to another. If the ray line interrogation is done at the precise instant when the stylet tip is reversing direction, there is effectively no motion and hence no visualization of the needle tip in the ultrasonic image. These problems are resolved by synchronizing the motion of the biopsy needle with the timing of the ray line Doppler interrogation. The drive signal for the motive mechanism 44 is illustratively shown as a sawtooth waveform in FIG. 5a, with turn-around of the mechanism occurring at times to, t1, t2, etc. These turnaround times are synchronized to the commencement of ensemble transmission, or to periods of conventional two-dimensional structural imaging performed between ray line Doppler interrogations. FIG. 5b is drawn in correspondence with the waveform of FIG. 5a, and illustrates the occurrence of stylet tip turn-around in synchronization with the beginning of every fourth ray line interrogation. In this example, turn-around occurs after the fourth ray line, the eighth, the twelfth, and so forth. With stylet tip motion synchronized in this manner, the deleterious Moire pattern effects and turn-around image dropouts can be remedied. In FIG. 1, the timing and control system 24 provides the ray line ensemble synchronizing pulse suitable for use by the oscillating mechanism 46.

In some applications, it may be desirable not to synchronize the motion at the needle tip with the doppler interrogation rate. If the two rates of interrogation and motion are known and unsynchronized, the Moire pattern will occur at a known intermodulation frequency between the two rates. This predetermined intermodulation frequency can be discriminated, as by detecting the frequency by filtering the Doppler data from frame to frame. When the predetermined frequency is detected in the Doppler image data, the location of the detection in the image may be marked on the image display to indicate the tip of the needle in the tissue being biopsied.

It has been found that the biopsy needle can be reciprocated over a wide range of frequencies. Audio frequencies have been found to be preferred for their ease of application, preferably frequencies of several hundred Hertz and most preferably below one hundred Hertz. For instance in a constructed embodiment a sequence of 52 ultrasound pulses were transmitted to interrogate a group of ray lines for Doppler information and to detect structure in a corresponding image sector area. The pulse rate used was 4 KHz. At the end of this pulse sequence the direction of travel of the stylet tip was reversed and the stylet moved in the opposite direction for the same time period. Dividing the pulse rate by the number of pulses corresponding to a full cycle of travel for the stylet, 104 pulses, gives a frequency of approximately 38.5 Hertz, the oscillating frequency for the stylet.

It has also been found desirable in certain applications to reduce the size and weight of the mechanism at the proximal end of the end of the needle in FIG. 3 may be undesirable for some users. In those applications the mechanism 46 of FIG. 1 may be housed in or attached to the ultrasound machine and connected to the proximal end of the member 42 by a thin sheathed cable similar to a speedometer cable. The mechanism within the ultrasound machine provides the necessary motion, which is carried to the stylet by the cable in the sheath. The user is thereby presented with a very light biopsy needle arrangement connected to the ultrasound machine only by a thin sheath.

It has further been found that the conventional color flow imaging system strongly emphasizes the flow characteristics in a structure by inserting areas of color into an image where flow is occurring. While highlighting flow, there is no representation of structure in such an image where flow is occurring, as the tissue structure is obscured by the color. This is undersirable in use of the present invention, where the user constantly desires to be able to view the mass which is to be biopsied as the needle tip approaches the mass. Instead of replacing and hence masking the structure of the mass with color as the needle tip approaches the mass, in a preferred embodiment the color representative of the needle tip location is used to modulate the display of the mass. Thus, as the needle tip approaches the mass, the image of the mass will turn color as the needle tip reaches the mass. The image of the mass is never obscured by color Doppler, instead, the image of the mass turns brightly colored as the needle tip reaches it. The center of the colored area is the location of the needle tip opening where the motion of the stylet tip is generating the Doppler response.

What is claimed is:

1. An ultrasonic biopsy needle imaging system comprising:
    a biopsy needle means including a hollow cannula, a removable member carried within the cannula, and motive means, coupled to said biopsy needle means, for reciprocating at least a portion of the tip of said biopsy needle means with motion of an electromechanically controlled displacement and velocity which is positionally detectable by Doppler signal interrogation; and
    an ultrasonic imaging system including Doppler signal interrogation means for detecting the motion of said tip, and means for generating a structural image of an interior region of a body in which said motion is locationally represented.

2. The ultrasonic biopsy needle imaging system of claim 1, further comprising a removable member carried within said cannula and extendable to the tip thereof, wherein said motive means is coupled to said removable member for reciprocating said removable member within said cannula.

3. The ultrasonic biopsy needle imaging system of claim 2, wherein said removable member reciprocates between a first position at which the distal end of said member is substantially aligned with the distal end of said cannula, and a second position at which the distal end of said member is retracted within said cannula with respect to said first position.

4. The ultrasonic biopsy needle imaging system of claim 3, wherein said removable member comprises a stylet.

5. The ultrasonic biopsy needle imaging system of claim 2, further comprising means for coupling motion produced by said motive means to said removable member.

6. The ultrasonic biopsy needle imaging system of claim 5, wherein said coupling means includes a sheathed cable.

7. The ultrasonic biopsy needle imaging system of claim 5, wherein said motive means is coupled to said removable member for reciprocating said member at an audio frequency.

8. The ultrasonic biopsy needle imaging system of claim 7, wherein said removable member is reciprocated at a frequency which is less than 1000 Hertz.

9. The ultrasonic biopsy needle imaging system of claim 8, wherein said removable member is reciprocated at a frequency which is less than 100 Hertz.

10. The ultrasonic biopsy needle imagining system of claim 1, wherein said motive means includes a solenoid.

11. The ultrasonic biopsy needle imaging system of claim 1, wherein said motive means includes a speaker-type moving coil.

12. The ultrasonic biopsy needle imaging system of claim 1, wherein said ultrasonic imaging system includes timing and control means for controlling said Doppler signal interrogation, and wherein said motive means is coupled to said timing and control means for energizing said motive means is synchronization with said Doppler signal interrogation.

13. The ultrasonic biopsy needle imaging system of claim 1, wherein said motive means reciprocates said tip of said biopsy needle means in substantially the longitudinal direction with respect to said cannula.

14. The ultrasonic biopsy needle imaging system of claim 1, wherein said ultrasonic imaging system further generates an image in which structure is locationally represented, and wherein said needle tip is locationally represented in said image by modulating said structural image with a color in the vicinity of the location of said needle tip in said image.

15. A method for imaging placement of a biopsy needle within an interior region of a body comprising the steps of:
    a. ultrasonically imaging the region which is to be biopsied with an ultrasonic imaging system which produces a structural image of said interior region and a locational representation of a motional characteristic of moving material within said region through Doppler signal interrogation of said region;
    b. inserting a biopsy needle, having means for controllably electromechanically reciprocating at least a portion of the tip of the needle, into the imaged region;
    c. interrogating the imaged region by said ultrasonic imaging system with ultrasonic Doppler signals; and
    d. developing a visual signal of the Doppler response to the motion of said reciprocating needle tip for locational display with respect to the ultrasonically image region.

* * * * *